US00PP28910P3

(12) United States Plant Patent
Gass

(10) Patent No.: US PP28,910 P3
(45) Date of Patent: Jan. 30, 2018

(54) ***HESPERALOE* PLANT NAMED 'MSWNPERED'**

(50) Latin Name: *Hesperaloe parviflora*
Varietal Denomination: MSWNPered

(71) Applicant: Ronald E. Gass, Glendale, AZ (US)

(72) Inventor: Ronald E. Gass, Glendale, AZ (US)

(73) Assignee: Camelot Nurseries Inc., Glendale, AZ (US)

( * ) Notice: Subject to any disclaimer, the term of this patent is extended or adjusted under 35 U.S.C. 154(b) by 49 days.

(21) Appl. No.: 14/999,472

(22) Filed: May 11, 2016

(65) Prior Publication Data

US 2017/0332536 P1 Nov. 16, 2017

(51) Int. Cl.
*A01H 5/02* (2006.01)

(52) U.S. Cl.
USPC ..... Plt./263.1
CPC ..... *A01H 5/02* (2013.01)

(58) Field of Classification Search
None
See application file for complete search history.

*Primary Examiner* — Anne Grunberg
(74) *Attorney, Agent, or Firm* — C. A. Whealy

(57) ABSTRACT

A new and distinct cultivar of *Hesperaloe* plant named 'MSWNPered', characterized by its relatively compact plant habit; vigorous growth habit; upright purplish red-colored peduncles; campanulate bright red-colored flowers; and good garden performance.

1 Drawing Sheet

Botanical designation: *Hesperaloe parviflora.*
Cultivar denomination: 'MSWNPered'.

CROSS-REFERENCED TO CLOSELY-RELATED APPLICATIONS

Title: *Hesperaloe* Plant Named 'MSWNPerma'
Applicant: Ronald E. Gass
Filed: May 11, 2016
Serial number: Ser. No. 14/999,471

BACKGROUND OF THE INVENTION

The present invention relates to a new and distinct cultivar of *Hesperaloe* plant, botanically known as *Hesperaloe parviflora* and hereinafter referred to by the name 'MSWNPered'.

The new *Hesperaloe* plant is a product of a planned breeding program conducted by the Inventor in Glendale, Ariz. The objective of the breeding program is to develop new freely flowering *Hesperaloe* plants with unique flower form and color.

The new *Hesperaloe* plant originated from an open-pollination of an unnamed selection of *Hesperaloe parviflora*, not patented, as the female, or seed, parent with an unknown selection of *Hesperaloe parviflora*, as the male, or pollen, parent. The new *Hesperaloe* plant was discovered and selected by the Inventor on Apr. 1, 2007 as a single flowering plant within the progeny of the stated open-pollination in a controlled environment in Glendale, Ariz.

Asexual reproduction of the new *Hesperaloe* plant by tissue culture since Apr. 10, 2010, in a controlled greenhouse environment in Waseca, Minn., has shown that the unique features of this new *Hesperaloe* plant are stable and reproduced true to type in successive generations of asexual reproduction.

SUMMARY OF THE INVENTION

Plants of the new *Hesperaloe* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'MSWNPered'. These characteristics in combination distinguish 'MSWNPered' as a new and distinct *Hesperaloe* plant:

1. Relatively compact plant habit.
2. Vigorous growth habit.
3. Upright purplish red-colored peduncles.
4. Campanulate bright red-colored flowers.
5. Good garden performance.

Plants of the new *Hesperaloe* can be compared to plants of the female parent selection. Plants of the new *Hesperaloe* differ from plants of the female parent selection in the following characteristics:

1. Plants of the new *Hesperaloe* are more compact than plants of the female parent selection.
2. Flowers of plants of the new *Hesperaloe* are bright red in color whereas flowers of plants of the female parent selection are yellow to salmon or coral in color.

Plants of the new *Hesperaloe* can be compared to plants of the *Hesperaloe parviflora* 'MSWNPerma', disclosed in U.S. Plant patent application Ser. No. 14/999,471 filed concurrently. Plants of the new *Hesperaloe* differ from plants of 'MSWNPerma' primarily in flower color as plants of 'MSWNPerma' produce flowers that are brownish red to dark purple in color.

Plants of the new *Hesperaloe* can also be compared to plants of *Hesperaloe funifera*×*Hesperaloe parviflora* 'Perfu', disclosed in U.S. Plant Pat. No. 21,728. Plants of the new *Hesperaloe* differ primarily from plants of 'Perfu' in flower color as plants of 'Perfu' have pink-colored flowers. Additionally, plants of the new *Hesperaloe* are more compact than plants of 'Perfu'.

BRIEF DESCRIPTION OF THE PHOTOGRAPHS

The accompanying colored photographs illustrate the overall appearance of the new *Hesperaloe* plant, showing the colors as true as it is reasonably possible to obtain in colored reproductions of this type. Colors in the photographs may differ slightly from the color values cited in the detailed botanical description which accurately describe the colors of the new *Hesperaloe* plant.

The photograph at the top of the sheet is a side perspective view of a typical plant of 'MSWNPered' grown in a container.

The photograph at the bottom of the sheet is a close-up view of a typical inflorescence of 'MSWNPered'.

DETAILED BOTANICAL DESCRIPTION

The aforementioned photographs and following observations, measurements and values describe plants of the new *Hesperaloe* grown during the spring in one-gallon containers in an outdoor nursery in Glendale, Ariz. and under cultural practices and conditions which closely approximate commercial production. During the production of the plants, day temperatures ranged from 30° C. to 35° C. and night temperatures ranged from 16° C. to 21° C. Plants were three years old when the photographs and the description were taken. In the description, color references are made to The Royal Horticultural Society Colour Chart, 2007 Edition, except where general terms of ordinary dictionary significance are used.

Botanical classification: *Hesperaloe parviflora* 'MSWNPered'.

Parentage:

*Female, or seed, parent*.—Unnamed selection of *Hesperaloe parviflora*, not patented.

*Male, or pollen, parent*.—Unknown selection of *Hesperaloe parviflora*, not patented.

Propagation:

*Type*.—By tissue culture.

*Time to initiate roots*.—About 56 days.

*Time to produce a rooted young plant, summer*.—About 77 days.

*Time to produce a rooted young plant, winter*.—About 105 days.

*Root description*.—Medium in thickness, fibrous; white to brown in color.

*Rooting habit*.—Freely branching; medium density.

Plant description:

*Plant form and growth habit*.—Perennial subshrub; upright plant habit; vigorous growth habit; leaves arranged in a basal rosette with a upright central flower stalk.

*Plant height, from soil level to top of inflorescence*.—About 108 cm.

*Plant height, from soil level to top of foliar plane*.—About 40 cm.

*Plant diameter* (*area of spread*).—About 62 cm.

Stem description:

*Internode length*.—About 4 mm.

*Aspect*.—Upright.

*Texture*.—Smooth, glabrous.

*Color*.—Close to 158D; leaves cover the stem.

Leaf description:

*Arrangement*.—In a basal rosette, whorled; simple; sessile.

*Length*.—About 45 cm.

*Width*.—At the apex, about 2 mm; mid-section, about 8 mm; at the base, about 4.7 cm.

*Shape*.—Lanceolate; concave.

*Apex*.—Acuminate; apices are sharply pointed.

*Base*.—Clasping the stem.

*Margin*.—Entire; filiferous with tough curly fibers.

*Texture, upper and lower surfaces*.—Smooth, glabrous; rigid and fibrous; longitudinally ridged; succulent.

*Venation pattern*.—Parallel.

*Color*.—Developing leaves, upper surface: Close to 146D. Developing leaves, lower surface: Close to 146C. Fully expanded leaves, upper surface: Close to 146C; at the base, close to NN155A; venation, close to 146C. Fully expanded leaves, lower surface: Close to 146B; at the base, close to NN155A; venation, close to 146B.

Flower description:

*Flower type, arrangement and flowering habit*.—Single campanulate flowers with flared flower segment apices; flowers arranged in terminal upright branched racemes; freely flowering habit with about 160 flowers per inflorescence at one time; flowers initially face upright and then face outwardly to slightly drooping with development.

*Natural flowering season*.—Continuous flowering during the spring and summer in Arizona.

*Flower longevity*.—Individual flowers last about five days on the plant; flowers not persistent.

*Fragrance*.—None detected.

*Inflorescence length, including peduncle*.—About 103 cm.

*Inflorescence length, section with flowers*.—About 28 cm.

*Inflorescence diameter*.—About 9 cm.

*Flower length*.—About 2.3 cm.

*Flower diameter*.—About 1 cm.

*Flower buds*.—Length: About 2 cm. Diameter: About 9 mm. Shape: Oblong. Color: Close to 46A.

*Flower segments*.—Quantity and arrangement: Six segments per flower arranged in two whorls. Length: About 2.1 cm. Width: About 6 mm. Shape: Elliptical. Apex: Acute; flared or reflexed. Base: Truncate. Margin: Entire. Texture, upper and lower surfaces: Smooth, glabrous; slightly succulent. Color: When opening, inner surface: Close to 53C to 53D. When opening, outer surface: Close to 53B. Fully opened, inner surface: Close to 182A; color does not change with development. Fully opened, lower surface: Close to 53B to 53C; color does not change with development.

*Peduncles*.—Length: About 49 cm. Diameter: About 8 mm. Strength: Strong. Aspect: Upright. Texture: Smooth, glabrous; slightly glaucous. Color: Close to 183D.

*Pedicels*.—Length: About 1.7 cm. Diameter: About 1 mm. Strength: Strong. Aspect: About 45° to 55° from peduncle axis. Texture: Smooth, glabrous. Color: Close to 53A.

*Reproductive organs*.—Androecium: Quantity per flower: About six. Filament length: About 1.1 cm. Filament color: Close to 47C to 47D. Anther shape: Oblong. Anther length: About 4 mm. Anther color: Close to 16C. Amount of pollen: Moderate. Pollen color: Close to 15B. Gynoecium: Quantity per flower: One. Pistil length: About 1.8 cm. Style length: About 9 mm. Style color: Close to 54C. Stigma appearance: Rounded. Stigma color: Close to NN155C. Ovary color: Close to 11C.

*Seeds*.—Seed development has not been observed on plants of the new *Hesperaloe*.

Garden performance: Plants of the new *Hesperaloe* have been observed to have good garden performance and to tolerate rain, wind and temperatures ranging from about −28° C. to about 48° C.

Pathogen & pest tolerance: Plants of the new *Hesperaloe* have been observed to be tolerant to pathogens and pests common to *Hesperaloe* plants.

It is claimed:

1. A new and distinct *Hesperaloe* plant named 'MSWN-Pered' as illustrated and described.

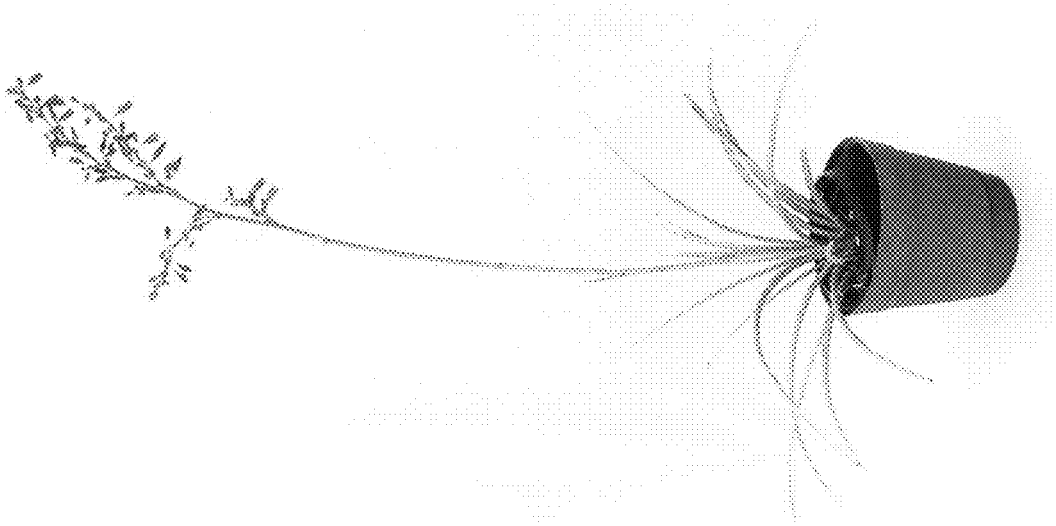
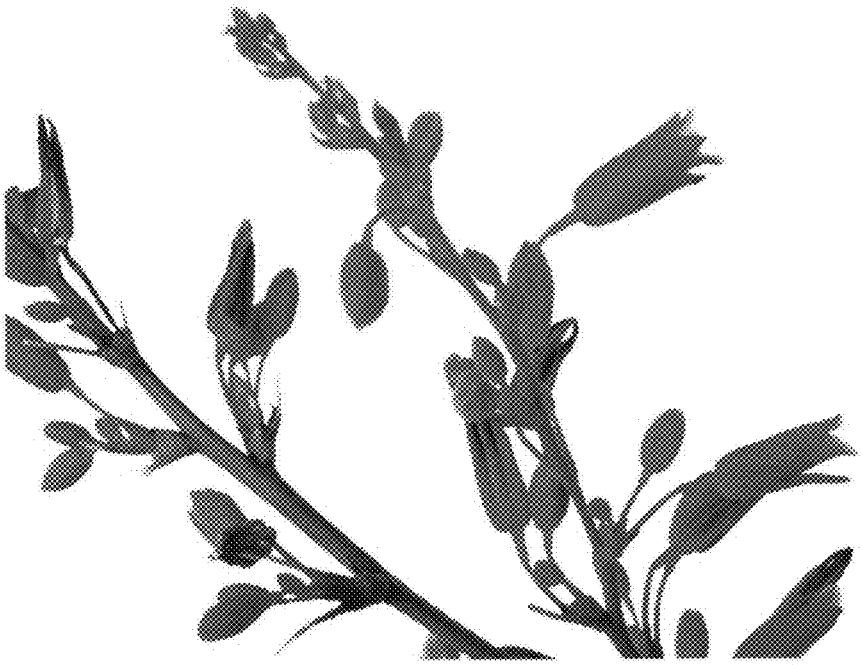

* * * * *